(12) United States Patent
Roy

(10) Patent No.: US 7,239,917 B2
(45) Date of Patent: Jul. 3, 2007

(54) VIPUL'S LIFETIME LIFELINE PERMANENT PACEMAKER AND IMPLANTABLE CARDIOVERTER-DEFIBRILLATOR

(75) Inventor: Vipul Narain Roy, c/o Dr Atul Roy, 18154 Trufle La., Boyds, MD (US) 20841

(73) Assignee: Vipul Narain Roy, New Delhi (IN)

( * ) Notice: Subject to any disclaimer, the term of this patent is extended or adjusted under 35 U.S.C. 154(b) by 552 days.

(21) Appl. No.: 10/642,813

(22) Filed: Aug. 19, 2003

(65) Prior Publication Data

US 2004/0044369 A1    Mar. 4, 2004

(51) Int. Cl.
*A61N 1/378* (2006.01)
(52) U.S. Cl. .................................................. 607/34
(58) Field of Classification Search ............ 607/4, 607/30, 34
See application file for complete search history.

(56) References Cited

U.S. PATENT DOCUMENTS

| 4,134,408 | A | * | 1/1979 | Brownlee et al. | 607/33 |
| 5,411,537 | A | * | 5/1995 | Munshi et al. | 607/33 |
| 5,725,559 | A | * | 3/1998 | Alt et al. | 607/5 |
| 6,070,103 | A | * | 5/2000 | Ogden | 607/60 |

* cited by examiner

*Primary Examiner*—George R. Evanisko
*Assistant Examiner*—Michael Kahelin

(57) ABSTRACT

A Permanent Pacemaker and Implantable Cardioverter-Defibrillator with a rechargeable battery with recharging facility This PPM/ICD has systems which can be programmed or serviced from a distant center.

2 Claims, 3 Drawing Sheets

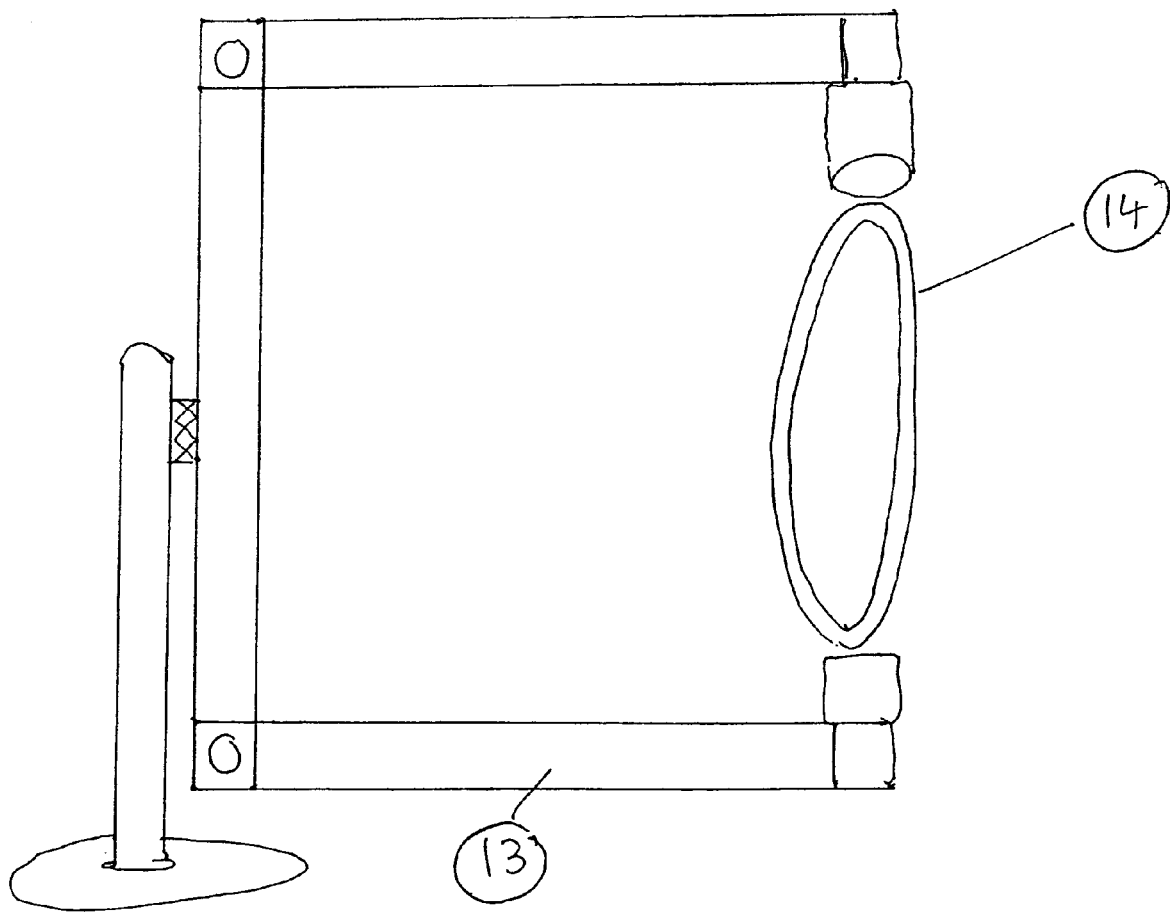
Fig 3.A

VIPUL'S LIFETIME LIFELINE PERMANENT PACEMAKER AND IMPLANTABLE CARDIOVERTER-DEFIBRILLATOR

CROSS REFERENCE TO RELATED APPLICATIONS

Herein reference to earlier related application on the same subject (Application No. 60/406,987 dated 30 Aug. 2002)

FEDERALLY SPONSORED RESEARCH OR DEVELOPMENT

Not applicable

REFERENCE TO SEQUENCE LISTING, A TABLE, OR A COMPUTER PROGRAM LISTING COMPACT DISK APPENDIX

Not applicable

The current level of technology of Permanent Pacemaker (PPM) and Implantable Cardioverter-Defibrillator (ICD) has two major problems.

BACKGROUND TO INVENTION (1) The battery of the pacemaker/ICD decides its life and change causes multiple problems such as:
   It requires an invasive (surgical) procedure and thus causes complications associated with it.
   Should infection develop it becomes a major problem as lead/leads/pocket etc will have to be sacrificed.
(2) The follow-up of the patient is a problem, due to lack of a programmer and skilled manpower in remote areas.

BRIEF SUMMARY OF INVENTION

This pacemaker/ICD will have a rechargeable battery and either a built-in generator or an external source will supply the energy for its recharge. Thus the same pacemaker box will continue to work and replacement will not be required (consequently replacement related problems, complications and additional cost will be avoided).

With every implant the patient to will receive dedicated programming software and a telemetry wand for remote programming. Thus it will reduce the cost of follow-up and it will be more useful for the patient. In remote areas patients will not be required to travel large distances. Such a central remote programming center can offer 24 hour service thus emergency programming will also be convenient.

BRIEF DESCRIPTION OF SEVERAL VIEWS OF DRAWING

Figure 1:
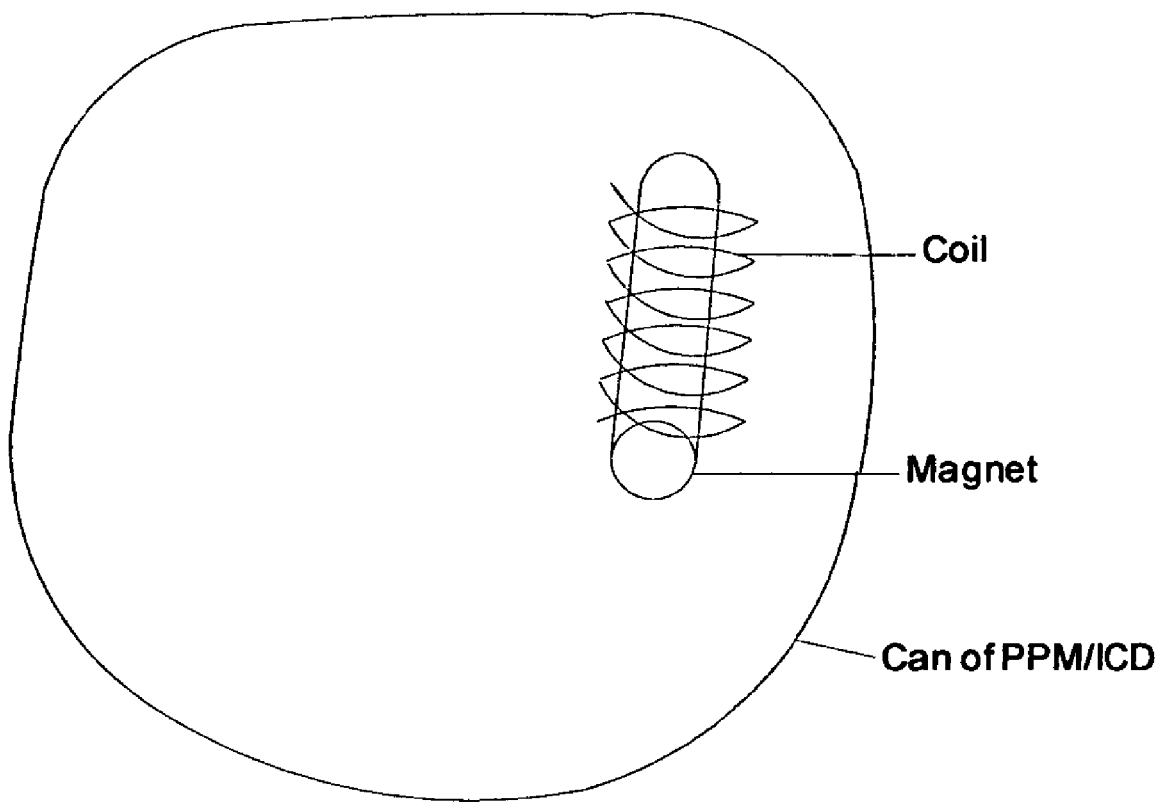

FIG. 1 It shows a PPM/ICD box with a built-in generator inside. The magnet is blue and it is surrounded by a coil (brown).

Figure 2:
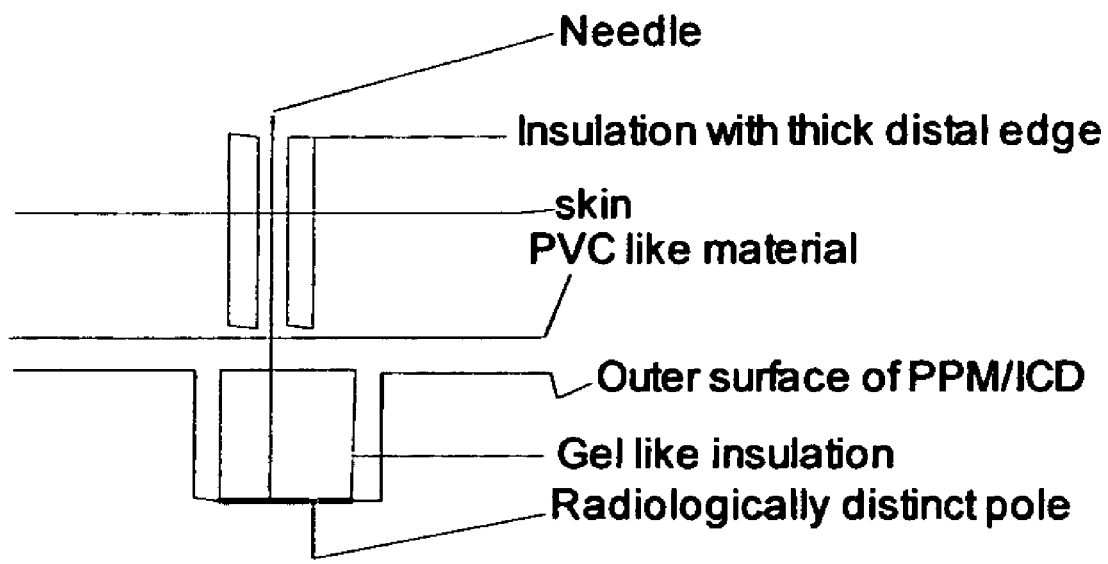

FIG. 2 It shows the radiologically distinct pole (to be localized on skin using fluoroscopy so that an insulated sterile needle can connect it to an outside power source) Gel like and PVC like material to ensure electrical insulation
   Note radiological distinct pole, can of PPM/ICD, gel like material and PVC like material will be in direct contact.
   The gap in figure has been shown for clarity.

FIG. 3A Note that it is prior art. It shows large radius circular coil and fluoroscopic facility from an angulated view.

13 U arm cath lab with fluoroscopic facility 14 large radius circular coil

The U or C arm cath-lab can rotate in any plane and offer fluoroscopy facility. This will help in desired alignment of large radius circular coil and the PPM/ICD box

DETAILED DESCRIPTION OF THE INVENTION

The PPM/LCD will have a rechargeable battery. Thus it will need energy for recharge, which will be supplied by:

(A) An internal generator in the following way

If in the box of PPM/ICD a small magnet is placed (which can rotate). A coil encircles this magnet. When the battery is nearing the discharge limit, patient will sit inside a large radius, circular coil (it also has a fluoroscopy facility, which helps in proper alignment with the PPM/ICD box), which can move in multiple planes; in a way that magnet in pacemaker/ICD aligns at center and perpendicular (with the help of fluoroscopy guidance). The PPM/ICD box will have radiological markers to help in alignment using the fluoroscopy facility of the large radius circular coil. When current passes through the large radius coil, the magnet starts rotating and generates a current to recharge the battery of pacemaker/ICD. It will also require one or more of the following changes:

Disable the magnet circuit or the magnet shield, for rest of circuit or rectangle becomes magnet on demand i.e. electrical magnet.

The arrangement of magnet and coil can also be the other way round i.e. magnet outside and coil inside.

Or Second Method:

(B) Alternatively at the body of the pacemaker two radiologically distinct poles, covered by a gel like insulation (Note gel like insulation is further reinforced by PVC like material) for recharging with an insulated, sterile outside source by following full aseptic technique.

When recharge is needed the skin over the box is handled with full aseptic technique. On skin local anesthesia is administered. Using fluoroscopy the exact location of the two radiologically distinct poles, are identified.

A thick needle is used to create a small hole here.

A fine needle is inserted which goes through the insulation up to the pole for recharging.

The above step is confirmed by fluoroscopy, that the needle has reached the exact spot.

An insulation is gently pushed on the needle. This insulation has thick terminal ends and it compresses the PVC and gel like insulation on the pole located on the PPM/ICD box.

Now an insulated connection is established to supply energy from an outside source.

Note that the PVC like insulation will not cover the entire surface of the can of PPM/ICD, so that it can be used as an anode or cathode.

This system will be useful as an alternative if the first suggested option the built-in generator malfunctions.

Remote Programming

The follow-up of the patient is a problem, due to lack of a programmer and skilled manpower in remote areas.

Note that a personal computer with multimedia and internet facility is available in almost all parts of the world.

With every implant the patient will receive
- A dedicated programming software, written on a non rewritable compact disk. His software will be able to work with any computer mouse/touch screen.
- A dedicated telemetry wand, which can be attached to the widely used IBM/Apple compatible or other computers.

The patient can go to any clinic where a doctor/skilled/semiskilled paramedic is available. He can get connected to the central programming center by an Internet/network connection. The software is on a non rewritable CD so it can not be changed or corrupted. The telemetry wand and software on CD will establish above connection using locally available personal computer for examination and reprogramming. It will make follow-up of the patient easy (widely available technology independent of an onsite programmer and trained PPM/ICD engineer), reduce cost (as no need to travel to distant healthcare locations), easy thus convenient for the patient and a center available 24 hours in case of emergency.

What is claim is:

1. A permanent pacemaker or cardioverter-defibrillator (PPM/ICD) system comprising:
   an implantable device adapted to be implanted in a patient having:
   a battery;
   a built-in electric power generator, said generator comprising a rotatable magnet and a coil encircling said magnet, said generator for generating power for recharging said battery;
   radiological markers; and
   two radiological distinct poles covered with insulating material, said poles adapted to connect to an outside power source if said power generator fails;
   an external large-diameter coil which is adapted to move in multiple planes and has fluoroscopic facility for alignment with said radiological markers, wherein said rotatable magnet is adapted to rotate and produce electrical current in said encircling coil from said magnet when the external coil is energized;
   a non-rewritable CD with programming software; and
   a telemetry wand for use with a personal computer and internet connection to allow a remote programming center to follow-up with said implantable device in accordance with the programming software contained on said non-rewritable CD.

2. The system of claim 1 wherein said software is adapted to be compatible with a remote programming center many miles from the patient via said internet connection.

* * * * *